US008804900B2

(12) United States Patent
Feuerlein et al.

(10) Patent No.: US 8,804,900 B2
(45) Date of Patent: Aug. 12, 2014

(54) METHOD AND DEVICE TO ASSIST IN DOSE REDUCTION OF X-RAY RADIATION APPLIED TO A PATIENT

(75) Inventors: Ute Feuerlein, Erlangen (DE); Jan Freund, Erlangen (DE); Sebastian Gehrsitz, Himmelstadt (DE)

(73) Assignee: Siemens Aktiengesellschaft, Munich (DE)

( * ) Notice: Subject to any disclaimer, the term of this patent is extended or adjusted under 35 U.S.C. 154(b) by 245 days.

(21) Appl. No.: 13/301,875

(22) Filed: Nov. 22, 2011

(65) Prior Publication Data
US 2012/0128121 A1 May 24, 2012

(30) Foreign Application Priority Data
Nov. 22, 2010 (DE) .................. 10 2010 044 218

(51) Int. Cl.
*H05G 1/60* (2006.01)
*H05G 1/64* (2006.01)
(52) U.S. Cl.
USPC .......................................... 378/16; 378/98.5
(58) Field of Classification Search
None
See application file for complete search history.

(56) References Cited

U.S. PATENT DOCUMENTS

| 7,254,623 | B1 | 8/2007 | Toth |
| 2007/0053503 | A1 | 3/2007 | Zelnik et al. |
| 2010/0040268 | A1 | 2/2010 | Boeing et al. |
| 2012/0213326 | A1* | 8/2012 | Walker et al. ............ 378/4 |

FOREIGN PATENT DOCUMENTS

| CN | 101004764 A | 7/2007 |
| DE | 198 09 738 A1 | 9/1999 |

OTHER PUBLICATIONS

Walker et al. (WO2011/048547), Scan Parameter Policy, Apr. 2011.*

* cited by examiner

*Primary Examiner* — Hoon Song
*Assistant Examiner* — Danielle Fox
(74) *Attorney, Agent, or Firm* — Schiff Hardin LLP

(57) ABSTRACT

In a method and x-ray device to assist in the reduction of the dose of x-ray radiation applied to the patient in the acquisition of at least one x-ray projection of the patient, a selected protocol is entered by a user into an x-ray device, the selected protocol being defined for the acquisition of the at least one x-ray projection and including a measure or measures for reduction of the dose of x-ray radiation to be applied to the patient in the acquisition of the at least one x-ray projection. The does reduction measure or measures in the selected protocol are automatically compared in a processor of the x-ray device, with the dose reduction measures that are installed at the x-ray device for reduction of the dose of x-ray radiation to be applied to a patient in the acquisition of the at least one x-ray projection. If the result of the comparison indicates a discrepancy between the dose reduction measure or measures in the selected, defined protocol and those installed in the x-ray device, at least one such measure installed at the x-ray device is visualized as a measure that can be set or activated by the user, that is not yet included in the selected protocol.

10 Claims, 2 Drawing Sheets

FIG 2

| Measure for dose reduction / Scan protocol | M1 | M2 | M3 | M4 | M5 |
|---|---|---|---|---|---|
| SP1 | ○ | ◍ | ○ | ● | ◍ |
| SP2 | ○ | ◍ | ○ | ○ | ⊛ |
| SP3 | ○ | ◍ | ○ | ○ | ⊛ |

○ included and activated
◍ available and can be activated
⊛ available but not recommended
● not available

METHOD AND DEVICE TO ASSIST IN DOSE REDUCTION OF X-RAY RADIATION APPLIED TO A PATIENT

BACKGROUND OF THE INVENTION

1. Field of the Invention

The invention concerns a method and an x-ray device to assist in the reduction of the dose of x-ray radiation applied to a patient in the acquisition of at least one x-ray projection of the patient. The invention also concerns a non-transitory computer-readable data storage medium encoded with programming instructions for implementing such a method.

2. Description of the Prior Art

In medical technology using imaging with x-ray radiation, for example in computed tomography, it is always sought to apply an optimally low dose of x-ray radiation to the patient to generate one or more images of tissue of the patient. However, a defined image quality must also be achieved in order to be able to answer clinical question at issue using the generated image or images, which requires a minimum dose.

In order to assist a user (of a computed tomography apparatus, for example) in the examination of defined tissue of a patient or in the acquisition of x-ray projections and the subsequent reconstruction of images of the defined tissue of the patient, known apparatuses have selectable scan protocols that include specific setting parameters for the respective examination or the respective acquisition of x-ray projections. These settings include the tube voltage, the tube current, the slice collimation etc. for the respective computer tomography apparatus. Measures to reduce the dose of x-ray radiation to be applied to the patient during the acquisition of x-ray projections are also included in the scan protocols. The scan protocols of a computed tomography apparatus that are included at the factory or by the manufacture, however, are only rarely adapted by the users of the computer tomography apparatuses to their own requirements and ideas, in particular with regard to the image quality.

Manufacturers of x-ray devices (such as computed tomography apparatuses) also normally introduce new or improved measures for dose reduction with each new version of apparatus type. Iterative reconstruction is an example of such a measure. If a user of the computed tomography apparatus receives a new apparatus, or even just a software version including new protocols, even though all protocols installed by the manufacturer are provided with all new or improved measures for dose reduction, it is most often technically impossible to automatically provide the existing protocols, that have already (previously) been adapted by the user to his own requirements (which protocols the user would like to continue to use) with the new or improved measures for dose reduction. Therefore the risk exists that the user at least occasionally makes no use of the new or improved measures for dose reduction, either due to a lack of knowledge as to how to manually embody them in the user's previously adapted protocols, or due to the lack of an automated adaptation of the protocols that user has previously adapted to his or her requirements before the software update.

SUMMARY OF THE INVENTION

An object of the invention is to specify a method, an x-ray device, and a data storage medium of the aforementioned type that assist a user in an improved manner in the reduction of the dose of x-ray radiation applied to a patient in an acquisition of at least one x-ray projection.

According to the invention, this object is achieved by a method to assist in the reduction of the dose of x-ray radiation applied to the patient in the acquisition of at least one x-ray projection of the patient, in which a selected protocol is entered by a user into an x-ray device, the selected protocol being defined for the acquisition of the at least one x-ray projection and including a measure or measures for reduction of the dose of x-ray radiation to be applied to the patient in the acquisition of the at least one x-ray projection. The does reduction measure or measures in the selected protocol are automatically compared in a processor of the x-ray device, with the dose reduction measures that are installed at the x-ray device for reduction of the dose of x-ray radiation to be applied to a patient in the acquisition of the at least one x-ray projection. If the result of the comparison indicates a discrepancy between the dose reduction measure or measures in the selected, defined protocol and those installed in the x-ray device, at least one such measure installed at the x-ray device is visualized as a measure that can be set or activated by the user, that is not yet included in the selected protocol.

The invention thus displays to a user of an x-ray device that measure or those measures installed at the apparatus or its software that lead(s) to an additional reduction of the dose of x-ray radiation to be applied to the patient during the acquisition of the x-ray projections of the defined tissue, whenever a defined protocol that he has selected by the user for the examination of that defined tissue of the patient (such as for the acquisition of x-ray projections of the defined tissue) does not exploit all measures available (installed) at the x-ray device for the reduction of that dose of x-ray radiation to be applied to said patient during the acquisition of said x-ray projections of said defined tissue. In this way the user is informed of the additional available measures for dose reduction of the patient, particularly in the case of the user intending to operate the x-ray device after a software update with protocols adapted to the user's requirements before the software update, or at an entirely new apparatus type of the x-ray device. The user is thus given the opportunity to activate these additional measures. An advantage is thereby achieved not only for the patient (in that a smaller dose of x-ray radiation is applied to the patient by the activation of newly available measures) but also for the user. Not only is the workflow simplified for the user, but also operating errors are reduced and the time cost of the application training to be conducted for the user given a software update or the change to a new apparatus type can be decreased.

The method can be applied to all protocols of the x-ray device so that, before its intended use, every protocol is always checked as to whether it is current with regard to the activation of measures for dose reduction for the patient. This also enables the user to supplement each of his or her protocols that have been individually adapted to his or her requirements with newly available measures for dose reduction, such that after an apparatus change or software update the adaptation of the user-defined or user-adapted protocols can take place successively without running the risk of overlooking protocols that are to be adapted.

According to a variant of the invention, in addition to the at least one dose reduction measure that can be set, the measure or measures already included in the protocol for the reduction of the dose of x-ray radiation that is to be applied to the patient given the acquisition of the at least one x-ray projection are visualized for the selected, defined protocol. In this way the user receives a quick overview of all possibilities that are available to the user for dose reduction for the examination of a patient.

According to another embodiment of the invention, for the selected, defined protocol for the at least one measure that can be set and for the measure or measures already included in the protocol for the reduction of the dose of x-ray radiation to be applied to the patient in the acquisition of the at least one x-ray projection, it is visualized whether the respective measure is activated, not activated, or is available but its activation is not advisable. In this way the user receives a quick overview not only of which possibilities for dose reduction are available to him or her for the examination of a patient, but also is given information about their activation. The respective dependencies of the different possibilities of dose reduction among one another as well as their effects on the achievable image quality thus are also taken into account. Depending on which measure or measures are already activated for dose reduction, different or additional measures for dose reduction can therefore be recommended, or be visualized as inadvisable.

For the selected, defined protocol, in an additional embodiment of the invention, a visualization is provided that identifies as unavailable one or more dose reduction measures in the selected protocol that is not provided (installed in) by the x-ray device. This has the advantage that, given defined (selected) does reduction measures that are expected to be available, the user is not left unaware of their actual unavailability. The designation "not available" also can be used to indicate that the measure for dose reduction in the selected, defined protocol is technically unwise.

According to another variant of the invention, the visualization upon the selection of the defined protocol takes place automatically, or manually upon an activation by a user. Preferably, upon the selection of a user-defined or user-adapted protocol, it would be appropriate to automatically produce the visualization of the possibilities for dose reduction.

The selected, defined protocol can be a scan protocol for operating a computed tomography apparatus.

According to embodiments of the invention, the x-ray device is a general purpose x-ray apparatus, a C-arm apparatus or a computed tomography apparatus of the type having a gantry.

BRIEF DESCRIPTION OF THE DRAWINGS

FIG. 2 shows a portion of a graphical user interface for operating an apparatus of the type shown in FIG. 1, in accordance with the invention.

DESCRIPTION OF THE PREFERRED EMBODIMENTS

Figure 1:
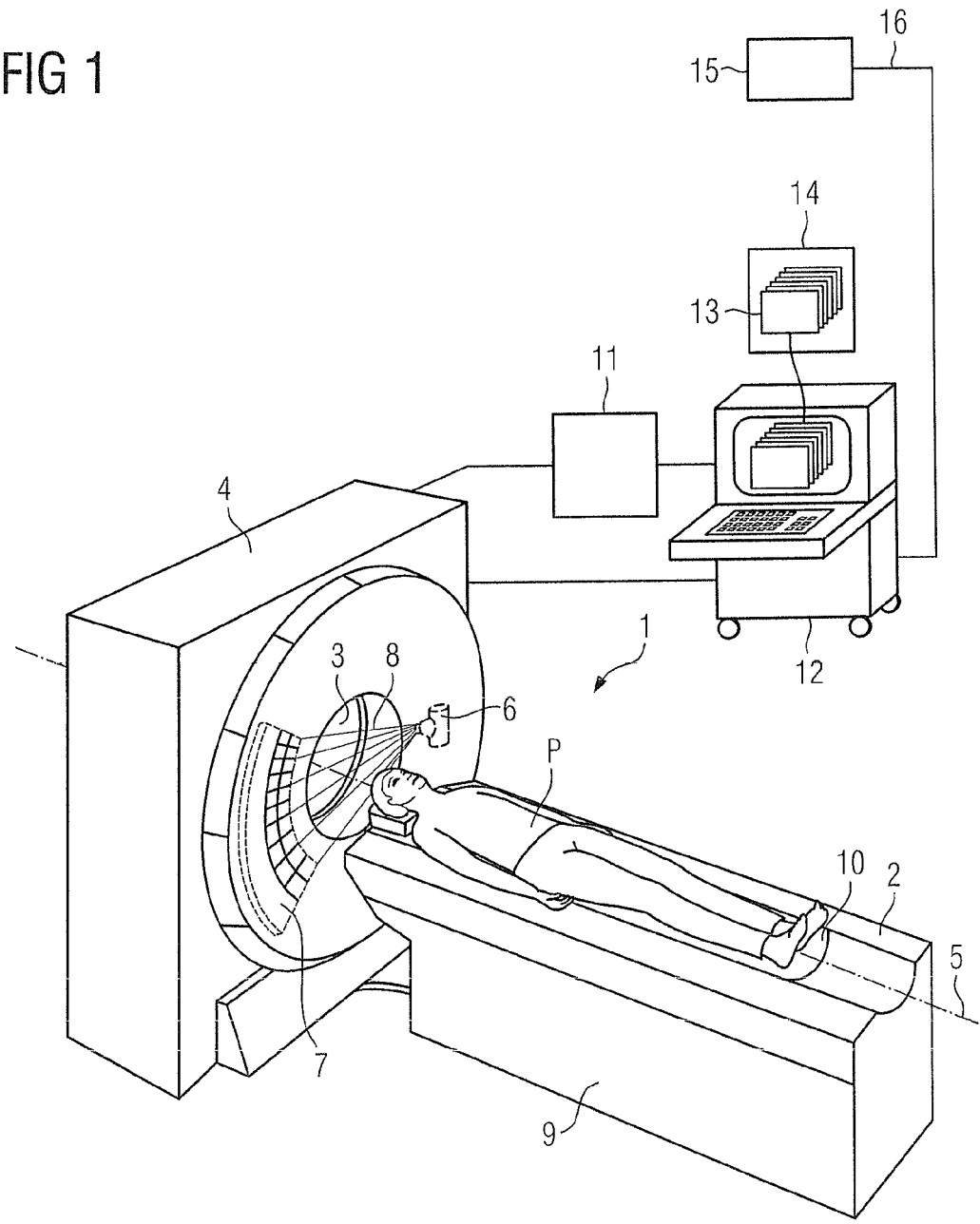
FIG. 1 schematically illustrates a computed tomography apparatus operable in accordance with the invention.

Shown in FIG. 1 is a computed tomography apparatus 1 that is suitable to execute the method according to the invention. The computed tomography apparatus 1 has a patient bed 2 to support a patient P to be examined. The computed tomography apparatus 1 also has a gantry 4 with a tube/detector system borne such that it can rotate around a system axis 5. The tube/detector system has an x-ray tube 6 and an x-ray detector unit 7 situated opposite one another. In operation, x-ray radiation 8 emanates from the x-ray tube 6 in the direction of the x-ray detector unit 7 and is detected by the detector unit 7.

The patient bed 2 has a bed base 9 on which is arranged a patient support plate 10 provided to actually support the patient P. The patient support plate 10 is adjustable relative to the bed base 9 such that the patient support plate 10 with the patient P thereon can be introduced into the opening 3 of the gantry 4 to acquire x-ray projections of the patient P, for example for a topogram or in a spiral scan. The computational processing of the x-ray projections, for example the generation of a topogram, a slice image or the reconstruction of a volume data set of a body region or tissue of the patient P based on the x-ray projections, takes place with an image computer 11 (schematically shown) of the computed tomography apparatus 1.

The computed tomography apparatus 1 has a computer 12 with which computer programs for operation and control of the computed tomography apparatus 1 are executed. The computer 12 does not need to be fashioned as a separate computer 12, but can be integrated into the computed tomography apparatus 1.

In the exemplary embodiment of the invention, a scan or an examination of defined tissue (such as the liver tissue of the patient P) should be implemented with the computed tomography apparatus 1, for which the user selects a defined scan protocol via a graphical user interface of the computer 12. The scan protocol has a number of acquisition parameters such as the tube voltage, the tube current, the slice collimation, the pitch etc., as well as measures for dose reduction for the scan of the liver tissue. As used herein, a scan is the acquisition of x-ray projections of the liver tissue from different directions with the tube/detector system.

Based on the acquired x-ray projections, in the exemplary embodiment of the invention slice images of the liver tissue of the patient P should be reconstructed with the image computer 11, the evaluation of which images forms the basis for a clinical diagnosis or the solution to a clinical question. For the generation of the slice images an optimally low dose of x-ray radiation should be applied to the patient P while maintaining an image quality required or, respectively, desired for the clinical diagnostic or, respectively, the solution to the clinical question.

For this purpose, the computer 12 is provided with a computer program 13 with which additional available measures that can be set for dose reduction should be displayed as necessary to the user of the computer tomography apparatus 1 in addition to the measures for dose reduction that are already included in the selected scan protocol for the scan of the liver tissue. The computer program 13 thereby realizes the method described in the following to assist in the reduction of the dose of x-ray radiation applied to a patient in the acquisition of at least one x-ray projection of the patient. The method can have been loaded into the computer 12 from, for example, a portable memory medium (a CD 14 or a memory stick, for example) or a server 15 as data medium via a network 16.

As was mentioned, the user selects a defined scan protocol for examination of the liver tissue, which scan protocol already has measures for dose reduction. According to the method according to the invention, the measures already included in the selected scan protocol for the reduction of the dose of x-ray radiation to be applied to the patient P given the acquisition of the x-ray projections are compared with the measures available at the computer tomography apparatus 1 for the reduction of the dose of x-ray radiation to be applied to a patient P given the acquisition of the x-ray projections. In particular, the comparison takes place specific to the protocol, meaning that the measures of the selected protocol for dose reduction are compared with the measures for dose reduction that are available for the examination of liver tissue.

If a discrepancy arises from the comparison such that measures available at the computer tomography apparatus 1 are not included in the selected scan protocol, this is displayed to the user via the graphical user interface.

In the exemplary embodiment of the invention, however, not only the new measures not included in the scan protocol and the measures already included in the scan protocol for dose reduction but also the measures for dose reduction that are not available for the selected examination type (thus presently for the examination of liver tissue) are visualized. FIG. 2 illustrates an example of the visualization using a section of the graphical user interface. Five measures M1 through M5 for dose reduction are available for different scan protocols SP1 through SP3 for the examination of liver tissue. The measures for dose reduction can, for example, be the control of the tube current of the tube/detector system depending on the rotation angle (which is known among other things as CARE Dose4D in products from Siemens AG); iterative reconstruction, which affects the acquisition parameter; the deactivation of the x-ray radiation depending on rotation angle (which is known, among other things, as X-CARE in products from Siemens AG); the automatic adjustment of the tube voltage (which is designated as, among other things, CARE xV in products from Siemens AG), etc.

The measures for dose reduction that are already included (and thus also already activated) in a scan protocol are visualized by a green traffic light. By placing a yellow traffic light, measures are visualized that are additionally available for the respective scan protocol but are not yet activated. Furthermore, measures that are not included in the respective scan protocol, are available for the respective scan protocol but are not recommended for activation are indicated for the respective scan protocol by placing a red traffic light. A dark traffic light identifies measures for dose reduction that are not available for the respective scan protocol.

For the selected scan protocol SP1, the measures M1 and M3 are already included (and thus activated) in the scan protocol; the measure M2 is available for activation; although the measure M5 is available for activation, its activation is not recommended; and the measure M4 is not available at all for the selected scan protocol. In the case of the present exemplary embodiment of the invention, the activation can moreover take place via a manipulation of the respective traffic light, for example with a mouse pointer of a computer mouse. The traffic light is thus essentially a "button". For thoroughness it is noted that a deactivation can also take place.

In this way the user of a computer tomography apparatus quickly receives an overview of all measures for dose reduction that are relevant to the selected scan protocol and, to reduce the dose of x-ray radiation that is to be applied to the patient P given the acquisition of the x-ray projections of the liver tissue, can activate the measures that are relevant to this insofar as this has not yet happened.

The visualization shown as an example in FIG. 2 can always take place automatically upon selection of a scan protocol. Alternatively, the visualization takes place as necessary via a manual activation on the part of the user.

Moreover, the visualization does not need to take place by means of traffic lights; rather, it can also take place with other graphical characters or symbols or by means of text fields.

The invention has presently been explained in an example of a scan protocol for the scan of liver tissue, but the invention is applicable to any other scan protocols to scan defined tissue of a patient.

The invention was described in the preceding for a computed tomography apparatus, but the invention is applicable in x-ray apparatuses in general, in particular also in C-arm x-ray apparatuses.

Although modifications and changes may be suggested by those skilled in the art, it is the intention of the inventor to embody within the patent warranted hereon all changes and modifications as reasonably and properly come within the scope of his contribution to the art.

We claim as our invention:

1. A method to assist in reducing a dose of x-ray radiation applied to a patient for acquisition of at least one x-ray projection of the patient, comprising:
    entering a selected protocol into a computerized control unit of an x-ray device, the selected protocol being defined for operating said x-ray device to acquire at least one x-ray projection of a patient by the x-ray device with an associated dose of x-ray radiation to which the patient is exposed, and said selected protocol including at least one algorithm for reducing a dose of x-ray radiation to be applied to the patient by operating the x-ray device in the acquisition of said at least one x-ray projection according to the selected protocol;
    in the computerized control unit, automatically comparing the dose reduction algorithm in the selected protocol to at least one dose reduction algorithm already installed in the x-ray device that would operate said x-ray device if said selected protocol had not been entered into said control unit; and
    if the comparison indicates a discrepancy between said at least one algorithm for dose reduction in the selected protocol and said algorithm for dose reduction already installed in the x-ray device, providing a visual indication to a user of the x-ray device that said algorithm for dose reduction already installed at the x-ray device is available and is not included in said selected protocol.

2. A method as claimed in claim 1 comprising also, if said discrepancy occurs, providing a visual indication of said measure for dose reduction that is included in said selected protocol.

3. A method as claimed in claim 1 comprising, upon the occurrence of said discrepancy, also providing a visual indication as to whether said measure installed at said x-ray device for a dose reduction is activated, or not activated, or is available but activation thereof is not recommended.

4. A method as claimed in claim 3 comprising also providing a visual indication as to whether said measure for dose reduction in said selected protocol is unavailable at said x-ray device.

5. A method as claimed in claim 1 comprising presenting said visualization at a graphical user interface of said x-ray device.

6. A method as claimed in claim 1 comprising generating said visualization automatically.

7. A method as claimed in claim 1 comprising generating said visualization upon a manual entry by a user upon selection of said selected protocol.

8. A method as claimed in claim 1 comprising selecting said selected protocol as a scan protocol for a computed tomography apparatus.

9. An x-ray device comprising:
    an x-ray imaging system;
    a computerized control device configured to operate said x-ray imaging system;
    said control device being configured to receive a user entry therein of a selected protocol defined for operating said x-ray imaging system to acquire at least one x-ray projection of a patient by the x-ray device with an associated dose of x-ray radiation to which the patient is exposed, said selected protocol including at least one algorithm for reducing the dose of x-ray radiation to be applied to the patient by operating the x-ray imaging system in the acquisition of said at least one x-ray projection according to the selected protocol;

said control device being configured to automatically compare the dose reduction algorithm in the selected protocol to at least one dose reduction algorithm already installed in the imaging system that would operate said x-ray imaging system if said selected protocol had not received said user entry of said selected protocol; and said control device being configured, if the comparison indicates a discrepancy between said at least one algorithm for dose reduction in the selected protocol and said algorithm for dose reduction already installed in the control device, to provide a visual indication that said algorithm for dose reduction already installed at the imaging system is available and is not included in said selected protocol.

10. A non-transitory computer-readable data storage medium encoded with programming instructions, said data storage medium being loadable into a computerized control device of an x-ray device, and said programming instructions causing said computerized control device to:

receive a selected protocol defined for operating the x-ray device to acquire at least one x-ray projection of a patient by the x-ray device with an associated dose of x-ray radiation to which the patient is exposed, said selected protocol including at least one algorithm for reducing the dose of x-ray radiation to be applied to the patient by operating the x-ray device in the acquisition of said at least one x-ray projection according to the selected protocol;

automatically compare the dose reduction algorithm in the selected protocol to at least one dose reduction algorithm already installed in the x-ray device, that would operate the x-ray device if said selected protocol had not been received by said control device; and if the comparison indicates a discrepancy between said at least one algorithm for dose reduction in the selected protocol and said algorithm for dose reduction already installed in the x-ray device, provide a visual indication that said algorithm for dose reduction already installed at the x-ray device is available and is not included in said selected protocol.

* * * * *